(12) United States Patent
Van Dyke et al.

(10) Patent No.: US 6,270,793 B1
(45) Date of Patent: *Aug. 7, 2001

(54) ABSORBENT KERATIN WOUND DRESSING

(75) Inventors: Mark E. Van Dyke, Fair Oaks Ranch; Scott F. Timmons; Cheryl R. Blanchard, both of San Antonio; Arlene J. Siller-Jackson, Helotes, all of TX (US); Robert A. Smith, Jackson, MS (US)

(73) Assignee: Keraplast Technologies, Ltd., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/528,893

(22) Filed: Mar. 20, 2000

Related U.S. Application Data

(63) Continuation-in-part of application No. 09/512,918, filed on Feb. 25, 2000, which is a continuation-in-part of application No. 09/394,782, filed on Sep. 13, 1999.

(51) Int. Cl.[7] ............................. A61F 13/00; A61L 15/00; A61L 15/16; A01N 37/18; A01N 38/00
(52) U.S. Cl. ........................ 424/443; 424/444; 424/445; 424/446; 424/447; 424/449; 514/2; 514/21
(58) Field of Search ................................... 424/443, 402, 424/444, 449, 445, 446

(56) References Cited

U.S. PATENT DOCUMENTS

| 4,135,942 | 1/1979 | Kikkawa | 106/155 |
|---|---|---|---|
| 4,357,274 | 11/1982 | Werner | 260/123 |
| 4,369,037 | 1/1983 | Matsunaga et al. | 8/127 |

(List continued on next page.)

FOREIGN PATENT DOCUMENTS

| 0454600A | 10/1991 | (EP) . |
|---|---|---|
| 56-129035 | 10/1981 | (JP) . |
| 5285374 | 11/1993 | (JP) . |
| 5285375 | 11/1993 | (JP) . |
| 6116300 | 4/1994 | (JP) . |
| 6293631 | 10/1994 | (JP) . |
| 6336499 | 12/1994 | (JP) . |
| 2106154C1 | 3/1998 | (RU) . |

OTHER PUBLICATIONS

JP Abstract 59051849, "Wound Covering Agent", Nitto Electric Ind Co., Mar. 1984.*
JP Abstract 59181158, "Covering Material for Wound", Nitto Electric Ind Co., Oct. 1984.*
RU Abstract 2106154, "Perforated Wound Dressing", Menzul V A., Mar. 1984.*
Blanchard, et al., U.S. application No. 09/057,161.
Southwest Research Institute Annual Report, 17–18, 21, 1997.
Technology Today, 16(3):9, 1995.
Timmons, et al., U.S. application No. 09/198,998.
Van Dyke, et al., U.S. application No. 09/330,550.
Yamauchi, et al., "Cultivation of fibroblast cells on keratin–coated substrata," Polymers of Tissue Engineering, 329–40, 1998.

Primary Examiner—Thurman K. Page
Assistant Examiner—Isis Ghali
(74) Attorney, Agent, or Firm—Timothy S. Corder; Stephen J. Moloney; Vinson & Elkins L.L.P.

(57) ABSTRACT

A hydratable, highly absorbent keratin solid fiber or powder capable of absorbing a large weight excess of water may be produced by partially oxidizing hair keratin disulfide bonds to sulfonic acid residues and reacting the sulfonic acid residues with a cation. The neutralized suspension can be filtered, washed, and dried, leaving keratin solid which can be shredded into fibers and further ground into powder. Addition of water to the solid produces a hydrogel. The powder or hydrogel may be useful as an absorbent material, as a therapeutic for skin, or as an excipient. The keratin materials can be incorporated into nonwoven films. Another use for the hydrogel is as a biocompatible viscoelastic filler for implant applications.

21 Claims, 2 Drawing Sheets

U.S. PATENT DOCUMENTS

| | | | |
|---|---|---|---|
| 4,439,417 | 3/1984 | Matsunaga et al. | 424/70 |
| 4,471,871 * | 9/1984 | Rockliffe et al. | 206/205 |
| 4,495,173 | 1/1985 | Matsunaga et al. | 424/70 |
| 4,570,629 | 2/1986 | Widra | 128/156 |
| 4,751,074 | 6/1988 | Matsunaga et al. | 424/70 |
| 4,839,168 | 6/1989 | Abe et al. | 424/74 |
| 4,895,722 | 1/1990 | Abe et al. | 424/71 |
| 4,959,213 | 9/1990 | Brod et al. | 514/21 |
| 5,047,249 * | 9/1991 | Rothman et al. | 424/543 |
| 5,134,031 | 7/1992 | Kagechi et al. | 428/373 |
| 5,258,043 | 11/1993 | Stone | 623/66 |
| 5,276,138 | 1/1994 | Yamada et al. | 530/357 |
| 5,358,935 | 10/1994 | Smith et al. | 514/21 |
| 5,712,252 | 1/1998 | Smith | 514/21 |
| 5,763,583 | 6/1998 | Arai et al. | 530/353 |
| 5,792,090 | 8/1998 | Ladin | 602/48 |
| 5,824,331 | 10/1998 | Usala | 424/424 |
| 5,932,552 | 8/1999 | Blanchard et al. | 514/21 |
| 5,948,432 | 9/1999 | Timmons et al. | 424/443 |
| 5,997,895 * | 12/1999 | Narotam et al. | 424/423 |

\* cited by examiner

ABSORBENT KERATIN WOUND DRESSING

RELATED APPLICATIONS

The present application is a continuation-in-part of U.S. patent application Ser. No. 09/572,918, entitled "Nonwoven Sheet and Film Containing Water Absorbent Keratin" filed Feb. 25, 2000 which in turn is a continuation-in-part of U.S. patent application Ser. No. 09/394,782 filed on Sep. 13, 1999.

FIELD OF THE INVENTION

The present invention is related generally to a keratin composition and method for making same. More specifically, the present invention relates to an absorbent keratin powder or fiber. In particular, the present invention includes a hydratable keratin solid which forms a hydrogel upon addition of water for use in various applications including nonwoven films, diapers, skin treatments, prosthetic devices, excipients, and the like.

BACKGROUND OF THE INVENTION

Absorbent materials are currently used to absorb body fluids such as urine, menses, and wound exudate. The absorbent materials are placed near the skin to serve this purpose. One class of products includes diapers, where the absorbent material can be derived from wood pulp, cellulosic fibers, or super absorbent, synthetically produced material. Diapers commonly have an inner core designed to absorb urine and water. The core is typically formed from a superabsorbent polymer dispersed in a larger amount of less absorbent material. The absorbent materials typically contained in the core are separated from the skin by at least one layer of material. The absorbent materials absorb urine and can become saturated. It is believed that some material from the absorbent core leaches from the wet absorbent and travels back to the skin. In the case of chemically treated absorbent materials and films, depending on the chemicals, the leachate may be irritating and is not believed to be beneficial. Skin contact with urine can also occur and result in irritation. This type of irritation may exacerbate diaper rash problems.

Other products which contain absorbent materials for use next to the skin include feminine hygiene products such as tampons and pads. These products serve to absorb menses. Another class of products using absorbent materials includes wound dressings, both those designed for humans, and dressings for veterinary use for application to wounds or skin irritations or disorders in animals. For specific applications, wound dressings preferably absorb exudate from wounds while keeping the wounds relatively moist to promote healing. In some applications, a gel may be desirable as a wound dressing, where the gel can maintain a moist wound environment, while absorbing excess exudate.

What would be desirable is an absorbent material formed from a natural product. What would be beneficial is a non-toxic product derived from natural sources that would cause no concern when leachate from the material contacts the body or the material itself contacts the body. What would be advantageous is a material that can absorb urine and, when wet, leach out a natural product that is beneficial with respect to diaper rash. What would be desirable is a material that can return a skin healing leachate to the skin. What would be desirable is a material that aids wound healing. What would be desirable is a hydrogel made of natural products formable by adding water to a powder or fiber.

SUMMARY OF THE INVENTION

The present disclosure addresses at least some of the deficiencies in the art by providing a hydratable, hydrogel-forming solid derived from a keratinous source such as hair, fur, human hair and the like. In the context of the present invention, the term "hydratable keratin" and "hydratable keratin material" is a keratin or keratin material that when hydrated can form a hydrogel. In certain embodiments, a hydrogel-forming solid as disclosed herein may absorb up to 5 to 20 times its weight in water to form a hydrogel. Such a solid, as well as the hydrogel formed from the solid will be useful in various applications such as use as an absorbent with skin healing properties when incorporated into diapers, feminine hygiene products, wound dressings, including both human and veterinary uses, as a soft tissue augmentation medium when used in subdermal implants, as a moisture containing agent in cosmetics, oils, lotions, or gels for use on the skin, in applications related to the healing of damaged skin, and as a pharmaceutical excipient for sustained release pharmaceutical applications.

A hydratable keratin solid may be made by methods that include providing a keratinous material, or keratin, having disulfide linkages and partially or substantially oxidizing the keratinous material with an oxidizing agent, for example, such that some disulfide linkages are cleaved and oxidized, forming hydrophilic sulfonic acid or cysteic acid residues. A preferred source of keratinous material is human hair, although the keratin may be obtained from hair or fur of animals including any mammal, or from finger or toenail material or from hooves, feet, beaks, skin, feather or horns. Human hair is a preferred source of keratin because of its ready availability from cuttings of barber and beauty shops, because it is expected to be less prone to cause undesirable immune or allergic reactions in a human, and because a keratin preparation may be made from the hair of a subject for whom the preparation will be used. This last advantage can be especially important in embodiments involving subdermal implantations.

It is well known in the art that keratins contain substantial sulfur, that is, the amino acid sequence of keratin contains a high proportion of cysteine residues as compared to proteins in general. These cysteines each include a sulihydryl moiety that is able to bond with another sulfhydryl moiety from another cysteine residue to form a disulfide bond. The second cysteine may reside within the same keratin molecule, or in another keratin molecule. These disulfide bonds are responsible for much of the tertiary and/or quaternary structure of this class of proteins. A suitable oxidizing agent is able to break this disulfide bond and to oxidize one or both of the sulfhydryl moieties so that they are no longer able to form a disulfide. Such an oxidation is a part of the process of forming the keratin products of the present disclosure. Preferred oxidizing agents include, but are not limited to peracetic acid, hydrogen peroxide, perborates, percarbonates, benzoyl peroxide, or ammonium sulfate peroxide. However, any suitable oxidizing agent known in the art can be used in the practice of the invention. After oxidation, the liquid oxidizing agent can be filtered from the oxidized keratin solid, and the solid may be washed to remove residual oxidizing agent, for example.

The resulting solid may then be suspended in a non-aqueous solvent and the pH may be adjusted upward with base—conveniently to at least neutral pH. Preferred solvents for this second solution do not include more than about 20 volume percent water, as the water may hydrolyze the peptide backbone during processing. Preferred solvents would include alcohols such as methanol, ethanol, or propanol, for example, and would also include non-aqueous polar, water-miscible solvents such as acetone and tetrahydrofuran, for example. An effective solvent should be able to solvate a Lewis base and should also be able to provide a medium able to keep the keratin sufficiently swelled to allow ionic associations or interactions between the base cations and anionic sulfonic acid groups in the keratin. Small amounts of water will assist in this regard, so blends of the aforementioned solvents in combination with water up to 20 volume percent may be used. Preferred bases include, but are not limited to sodium hydroxide, potassium hydroxide and ammonium hydroxide, which, as is known in the art, would yield or produce sodium, potassium and ammonium cations, respectively, upon entering solution.

The keratin suspension may be heated, and is preferably heated to boiling for a time sufficient to swell the keratin. The keratin suspension may be stirred without heat for a longer period of time to allow a more complete association or reaction between the sulfonic acid groups and the base cations. The continued reaction time at or near room temperature, or even below room temperature while stirring is contemplated by the inventors to allow the base cations to approach and bind to the keratin anionic sites with a lower incidence of peptide backbone degradation that could occur with continued boiling. The cations for use in the present invention, therefore, must be able to interact with the anionic cysteic groups in the keratin material. The use of the term "cations" or "monovalent cations" in the present disclosure and claims is indication of those cations that are able to do so. After a sufficient reaction time, the keratin solid may be removed from the suspension by filtration, for example, and dried, leaving a solid salt formed of the keratin sulfonic acid or cysteic acid groups and base cations. This solid may be shredded into a fibrous form and/or ground into a finely divided powder. This solid may be used in certain embodiments, or it may be hydrated by adding water, for example, and the hydrogel, or viscoelastic hydrogel thus formed may be used in certain embodiments.

In certain embodiments, an absorbent keratin layer may be incorporated into various absorbent articles such as a disposable diaper, a wound dressing, or feminine hygiene product, by adsorbing or coating a keratin solid or hydrogel onto a layer of the article, by impregnating a component of such an article, or by associating a keratin material with a nonwoven layer of such an article. In certain embodiments an absorbent keratin powder may be applied directly to skin to absorb moisture and inhibit rashes or chafing, such as diaper rash, for example. A hydratable keratin solid of the invention may have an absorbency of 1, 5, 10, 15 or even up to 20 times its weight in water. The absorbency may be adjusted by, for example, varying the degree of oxidation of the keratin in the process. It may thus provide a substitute or a supplement for products such as talc and cornstarch. The inventors have demonstrated, for example, that a fibrous or powdered form of solid keratin material as described herein can absorb about 10 times its weight in water in about 10 seconds.

The hydratable keratin solids as described herein form a hydrogel or a viscoelastic hydrogel upon application of water, and also are contemplated to contain skin healing peptides associated with the keratin, which may leach out of the keratin products when wet. The keratin products thus provide an added benefit, in addition to water absorbency, that is, healing or soothing peptides are also released that may have beneficial effects on the skin of a user of the products. This property offers certain benefits in embodiments such as wound dressings, as well as cosmetics, gels or lotions for application to the skin.

In certain embodiments a keratin absorbent as disclosed herein may be used as a wound dressing material to absorb wound exudate by direct application, or by incorporation into a dressing. The solid, hydratable forms of keratin offer certain advantages in such applications because they may be stored as dry powders or fibers and hydrated to form a gel in the field, or only as needed, for example. Medical applications, such as wound exudate management or drug release, can make use of the keratin material in absorbent powder, fiber, woven fiber, or felt form.

The keratin hydrogel is also believed to be suitable for use as an implant filler, for example, used to fill a breast implant, or to augment soft tissue for cosmetic, reconstructive or aesthetic reasons, or in a tissue expander application. The keratin product may also be used in cosmetics to retain moisture next to the skin. The performance of cosmetics which reduce the greasy appearance of skin can be enhanced through the use of moisture absorbent keratin material as an additive or base ingredient, for example, in a cosmetic formulation. The keratin absorbent and hydrogel can also be used for a variety of tissue engineering applications. Both materials may act as biocompatible scaffolds that provide a mitogen, the keratin peptide, to the cellular components of a tissue-engineered implant.

The present invention may be described, therefore, in certain aspects as a composition comprising a hydratable keratin solid, wherein the solid comprises a keratin where at least a portion of the cysteic groups of the keratin are ionically or electrostatically associated with, or may be ionically bound to cations. As used herein, ionically bound or ionically associated would have their ordinary meaning as is known in the art, and would include the electrostatic attraction between an anion and a cation, and would include such interactions directly, such as through formation of ionic bonds, and interactions through intermediary bipolar moieties, for example. A cysteic group would include cysteine and derivatives of cysteine including cysteine and cysteic acid or sulfonic acid. As used herein, cysteic acid and sulfonic acid denote a cysteine side chain in which the terminal sulfur is bonded to three oxygen atoms to produce the sulfonic acid ion, $SO_3^-$, or the acidic form, $SO_3H$. In certain embodiments, a portion of the cysteic groups are oxidized to sulfonic acid or cysteic acid groups. Sulfonic acid or cysteic acid groups may comprise a significant portion of the total cysteic groups and in some embodiments the sulfonic acid groups may constitute a major portion of the total cysteic groups. The extent of the oxidation may be adjusted by adjusting certain parameters of the oxidation reactions, such as temperature, concentration of oxidizing agent, and time of reaction, for example, to achieve a product with certain desired properties, such as absorbency or resiliency, for example.

In certain embodiments, therefore, the present invention may be described as a hydratable keratin solid made by a process comprising oxidizing a portion of the cysteic acid groups of a keratin to obtain a keratin having oxidized cysteic groups, and contacting the keratin having oxidized cysteic groups with monovalent cations under conditions effective to form ionic associations or ionic bonds between at least a portion of the oxidized cysteic groups and the cations.

In some embodiments, the hydratable keratin solid is made by a process comprising oxidizing at least a portion of the cysteic acid groups of a keratin to obtain a keratin having oxidized cysteic groups, and contacting said keratin having oxidized cysteic groups with monovalent cations under conditions effective to form ionic associations or ionic bonds between a substantial portion of said oxidized cysteic groups and said cations. The oxidation may comprise placing the keratin in a solution containing a concentration of an oxidizing agent effective to oxidize a portion of the cysteic acid groups. The portion of oxidized cysteic groups may be a major portion of the total cysteic acid groups.

In certain embodiments of the present invention, the oxidation comprises placing the keratin in a solution containing a concentration of hydrogen peroxide, peracetic acid, perborates, percarbonates, benzoyl peroxide or ammonium sulfate peroxide effective to oxidize a portion of the cysteic groups.

The process of the present invention may further comprise heating the keratin solid containing oxidized cysteic groups in a solvent solution containing a dissolved base, wherein the base produces the monovalent cations in the solution. The solvent solution may comprise a solvent selected from methanol, ethanol, propanol, ether, tetrahydrofuran (THF), acetone, propylene glycol, 1,4-dioxane, and glycol ether, or combinations of these with up to 20 volume percent water. In certain embodiments the process further comprises removing the solution from the heat and stirring for a time effective to form ionic bonds between the cysteic groups and cations produced by the base. The process may also further comprise drying the keratin solid, such as by drying a solid or solution under vacuum.

Another aspect of the present invention is a composition comprising a keratin hydrogel wherein the hydrogel is produced by adding water to a composition comprising a hydratable keratin solid, wherein the solid comprises a keratin where at least a portion of the cysteic groups of the keratin are ionically bound to cations. In some embodiments, the composition of the present invention comprises a keratin viscoelastic hydrogel produced by adding water to a composition comprising a hydratable keratin solid, wherein the solid comprises a keratin where a portion of the cysteic groups of the keratin are ionically bound to or associated with cations.

Another aspect of the present invention is a process for making a hydratable keratin solid comprising: (1) oxidizing keratin in a first solution comprising a soluble oxidizing agent, such that a portion of the disulfide bonds of the keratin are oxidized to form sulfonic acid residues, to obtain an oxidized solid fraction; (2) separating the oxidized solid fraction from the first solution; (3) contacting the oxidized solid fraction with a second, basic solution comprising a monovalent cation dissolved in a solvent or solvent mixture; (4) maintaining the second solution containing the oxidized solid fraction and the monovalent cations for a time and at a temperature effective to allow an interaction between the sulfonic acid residues and the monovalent cations to obtain a salt solution of the keratin and the monovalent cation; and (5) substantially removing the solvent from the salt solution to obtain a pure hydratable keratin solid.

The process may also further comprise adjusting the pH of the second solution, to obtain a substantially neutral solution. In some embodiments, the keratin is obtained from hair, fur, skin, feet, beaks, horns, hooves or feathers and is preferably obtained from human hair.

In some embodiments, the keratin is oxidized by suspending the keratin in a solution of a suitable oxidizing agent such as one selected from the group consisting of hydrogen peroxide, peracetic acid, perborates, percarbonates, benzoyl peroxide, and ammonium sulfate peroxide, in a concentration of between about 1 and about 35 weight/volume percent. In various embodiments, the keratin is oxidized by suspending the keratin in a solution of an oxidizing agent selected from the group consisting of hydrogen peroxide, peracetic acid, perborates, percarbonates, benzoyl peroxide, and ammonium sulfate peroxide, in a concentration of about 1, or about 2, or about 3, or about 4, or about 10, or about 15, or about 20, or about 30, or about 32, or about 35 weight/volume percent. As used herein the term weight/volume percent refers to a solution in which the concentration is determined in weight percent, that is then diluted into a particular volume, arriving at a weight/volume percent. For example, in order to arrive at the oxidant solutions described herein a "stock solution" at fairly high concentration is diluted in water. As an example, hydrogen peroxide may be purchased as a 30 weight % solution (30 grams of peroxide per 100 grams of solution). To make 1 liter of a 2% solution of this, one would dilute 66.7 mL of the 30 weight % stock solution in 933.3 mL of water. The net effect is to cut the stock solution 15-fold (from 30 down to 2%). This ratio is a weight to volume ratio, so the resulting solution is described as 2 weight/volume %.

In some embodiments, the keratin is oxidized by suspending the keratin in a solution of a suitable oxidizing agent, such as one selected from the group consisting of hydrogen peroxide, peracetic acid, perborates, percarbonates, benzoyl peroxide, and ammonium sulfate peroxide, in a concentration of between about 1 and about 35 weight/volume percent, at a temperature between about 0° C. and about 100° C. In other embodiments the temperature is between about 4° C. and about 90° C., or between about 20° C. and about 100° C., or between about 80° C. and about 100° C. In other embodiments, the temperature is about 4° C., or about 90° C., or about 100° C.

The present invention may also include the process wherein the keratin is oxidized by suspending said keratin in a solution of an oxidizing agent selected from the group consisting of hydrogen peroxide, peracetic acid, perborates, percarbonates, benzoyl peroxide, and ammonium sulfate peroxide, in a concentration of between about 1 and about 35 weight/volume percent, at a temperature between about 0° C. and about 100° C. for a period of between 0.5 and about 24 hours, or in a concentration of oxidizing agent of between about 1 and about 35 weight/volume percent, at a temperature between about 0° C. and about 100° C. for a period of between 1 and about 2 hours, or for between about 2 and about 4 hours, or for between about 1 and about 4 hours, or for a period of about 10 hours.

More specifically, the present invention may include oxidizing the keratin by suspending the keratin in a solution of between about 1 percent to about 32 percent peracetic acid at a temperature between about 0° C. and about 100° C. for between about 0.5 and about 24 hours, or by suspending the keratin in a solution of about 1 percent peracetic acid at a temperature between about 0° C. and about 100° C. for between about 0.5 and about 24 hours, or by suspending the keratin in a solution of between about 4 percent peracetic acid at a temperature of about 4° C. for 24 hours, or by suspending the keratin in a solution of about 4 percent peracetic acid at room temperature for about 24 hours, or by suspending the keratin in a solution of about 4 percent peracetic acid at about 90° C. for about 10 hours, or by suspending the keratin in a solution of about 4 percent peracetic acid at a temperature between about 20° C. and about 100° C. for between about 1 and about 4 hours, or by suspending the keratin in a solution of about 4 percent peracetic acid at a temperature between about 80° C. and about 100° C. for between about 1 and about 2 hours, or even by suspending the keratin in a solution of about 2 percent peracetic acid at a temperature between about 0° C. and about 100° C. for about 2 hours.

A second solution in the process of making the disclosed compositions, wherein the second solution contains the oxidized solid fraction and monovalent cations may be heated, and may also be boiled for between about 0.5 hours and about 12 hours, for between about 0.5 hours and about 3 hours, or for about 1 hour. Once said solution is boiled, the solution may be allowed to continue reacting while being stirred after removal of the heat. Alternatively, the solution may be stirred and allowed to react without the application of heat, or of boiling temperatures. In certain embodiments, the solution is allowed to react at a temperature of between about 15° C. and about 30° C. for a period of between about 1 and about 24 hours, or at a temperature of between about 20° C. and about 25° C. for a period of between about 1 and about 5 hours, or at room temperature for a period of about 5 hours. In certain preferred embodiments the solution is heated to the boiling point of the solvent and boiled for 2 hours.

Certain processes as described herein are effective to produce a hydratable keratin solid, and it is an embodiment of the present invention that those solids may be hydrated by the addition of water to obtain keratin hydrogels, or even viscoelastic keratin hydrogels. The terms hydrogel and viscoelastic hydrogel, as used herein, are meant to have the art recognized definition, and could be described as absorbing water such that the water cannot be removed by mechanical methods such as pressure or centrifugation. Viscoelastic hydrogels would also be defined as gels that display non-Newtonian fluid properties.

In certain embodiments the present invention may be described as a disposable diaper that includes a hydratable keratin solid, or a diaper which incorporates a hydratable or absorbent keratin solid. A hydratable keratin solid may be coated on a layer of the diaper, either a layer next to the skin of a wearer, or a layer separated from the skin of a wearer by a water permeable layer. In certain embodiments a hydratable keratin solid may be associated with a nonwoven layer of a diaper, or may be impregnated into a layer of a disposable diaper, or it may be contained in an inner absorbent core.

In certain alternative embodiments, the present invention may be described as a feminine hygiene product, or a wound dressing that includes a hydratable keratin solid. As was described for use in diapers, a hydratable keratin may be coated on a layer of a product, associated with a nonwoven layer of a product, or even impregnated into a layer of a product or contained in an absorbent core. Exemplary products would include wound dressings, tampons, and sanitary pads. Wound dressings include absorbent wound dressing, that is dressing capable of, but not limited to, absorbing wound exudate and blood. Absorbent dressings include, but are not limited to, adhesive bandages. Adhesive bandages typically comprise an absorbent pad, a backing and a pressure sensitive adhesive to maintain the dressing in place. In one aspect of the present invention, an absorbent wound dressing comprising hydratable keratin is an absorbent pad of an adhesive bandage. In one embodiment, the hydratable keratin in such an absorbent pad is in a nonwoven film.

Certain embodiments of the invention may be described as methods for promoting healing of skin in a subject including a human or an animal having damaged skin, including providing an absorbent, keratin material, wherein a portion and preferably a substantial or major portion of the cysteic groups of said keratin are oxidized and wherein water soluble peptides are associated with the keratin, wherein at least some of said peptides can leach out from said keratin upon application of water, and wherein said peptides promote healing of damaged skin; and disposing the absorbent keratin material near damaged skin, such that moisture causes at least some of said peptides to leach out of said keratin and to contact said skin. The method may be practiced with animal or human subjects, such that either animal or human skin is healed by this method. The practice of the method for promoting skin healing as described herein may include the treatment of damaged skin including, but not limited to diaper rash, burn, sunburn, cut, abrasion, puncture, a sore, bed sore, ulcer, diabetic ulcer, irritated skin, surgical incision, skin graft donor site, or wrinkled skin. The keratin material may be incorporated in a nonwoven film. The nonwoven film may comprise synthetic polymer webs and may also comprise natural materials such as cotton. It is understood that in the practice of such embodiments, the wound of the subject being treated may exude or excrete moisture and that the absorption of such moisture by said keratin may cause the release of water soluble peptides from keratin products of the present invention.

In certain embodiments the present invention may be described as a method for promoting skin healing, in particular in those embodiments in which a keratin solid or hydrogel as described herein, such as a keratin solid or hydrogel in which the keratin is obtained from human hair, for example, is contained in, or forms a portion of a cream, lotion, or gel for application to skin, hair, lips, or nails, for example. Such formulations can offer various advantages such as moisturizing the skin, or inhibiting loss of moisture from the skin, as well as providing the healing effects of peptides that may leach from the keratin containing product. Such creams, lotions and gels may be applied to damaged skin, such as dry, burned, sunburned, wrinkled, cut, scraped, chapped, irritated, ulcerated or otherwise damaged skin or other tissue.

One aspect of the present invention is a nonwoven film composition comprising a synthetic polymer and a keratin material, wherein the keratin material has been oxidized and contains sulfonic acid groups. The keratin material may be oxidized keratin material that has not undergone the ion exchange process or may be oxidized keratin that has undergone the ion exchange process to form a hydratable keratin. In the latter, the sulfonic acid groups of the hydratable keratin are associated with monovalent cations. The keratin materials may also be associated with pharmaceutical agents which may be in the form of polar compounds which are capable of binding or otherwise associating with the keratin. Such a pharmaceutical agent is aspirin. The synthetic polymer may be, but is not limited to, $\alpha$-olefins, acrylates, urethanes, acetates, nylons, esters, and copolymers thereof. An $\alpha$-olefin is considered to be any monomer containing an $\alpha$-double bond. The nonwoven composition may also further comprise a natural material which may be, but is not limited to, cotton. In some embodiments of the invention, the nonwoven composition is a laminate, which may be, but is not limited to, a tri-laminate comprising two outer layers of synthetic polymer and a middle layer of keratin material. The keratin material in the middle layer may be partially exposed by openings in the two outer nonwoven synthetic polymer layers. In some embodiments of the invention the synthetic polymer layers are nonwoven webs of polymer fibers. In other embodiments, the synthetic polymer layers are woven webs of polymer fibers.

Another aspect of the invention is a nonwoven tri-laminate composition comprising a middle layer of a keratin material between two outer layers of synthetic polymer material. The synthetic polymer may be in the form of a nonwoven web. The keratin material may be oxidized keratin that contains sulfonic acid residues. The oxidized keratin may be subjected to ion exchange such that the keratin material is a hydratable keratin material. The keratin material may be associated with pharmaceutical agents, which may be in a cationic form. The synthetic polymer may be, but is not limited to, α-olefins, acrylates, urethanes, acetates, nylons, esters, and copolymers thereof. The nonwoven composition may also further comprise a natural material which may be, but is not limited to cotton.

One aspect of the invention is a process for making a nonwoven film. In one embodiment a keratin material is applied to a first nonwoven web layer of synthetic polymer. A second nonwoven web layer of synthetic polymer is applied over the keratin material so as to form a tri-laminate composition with two outer layers of nonwoven synthetic polymer web and a middle layer of keratin material. Another aspect of the invention is a product made by the above described process. The keratin material may be oxidized keratin that contains sulfonic acid residues. The oxidized keratin may be subjected to ion exchange such that the keratin material is a hydratable keratin material. The keratin material may be associated with pharmaceutical agents, which may be in a cationic form. The synthetic polymer may be, but is not limited to, α-olefins, acrylates, urethanes, acetates, nylons, esters, and copolymers thereof. The nonwoven composition may also further comprise a natural material which may be cotton. The keratin material in the middle layer may be partially exposed by openings in the two outer nonwoven synthetic polymer layers.

Other aspects of the present invention include wound dressings, diapers and feminine hygiene products which comprise a nonwoven film made from a synthetic polymer and a hydratable keratin material. In certain embodiments, the non-woven film of the present invention may be next to the skin or other epithelial layer of a subject, or may be separated from the skin or other epithelial layer of a subject by a water permeable layer, which may be a non-wetting water permeable layer. In certain embodiments a hydratable keratin solid may be associated with a nonwoven layer of a diaper, or may be impregnated into a layer of a disposable diaper, or it may be contained in an inner absorbent core. These products may be laminate compositions, which may be tri-laminates comprising two outer layers of synthetic polymer and a middle layer of keratin material. The keratin material in the middle layer may be partially exposed by openings in the two outer nonwoven synthetic polymer layers. In some embodiments of the invention the synthetic polymer layers are nonwoven webs of polymer.

Creams, lotions, or gels of the present invention may incorporate or replace other ingredients known in the art, including, but not limited to oleaginous, emulsifiable, emulsion base, or water-soluble ointment bases as are well known in the pharmaceutical arts. Oleaginous bases that may be combined with the keratin compositions include ointments containing white wax and/or white petrolatum, ointments containing yellow wax and petrolatum, cetyl esters wax, oleic acids, and paraffins. Absorbent ointment bases or emulsifiable bases that may be used include those containing anhydrous lanolin, or combinations of cholesterol, stearyl alcohol, white wax and petrolatum, for example. Emulsion bases and components that may be used include ointments containing cetyl alcohol, and cold creams such as those containing cetyl esters wax, white wax, mineral oil, sodium borate and water, for example. Other ointments of the present invention may contain glyceryl monostearate, lanolin, stearic acid, or a combination of methylparaben, propylparaben, sodium lauryl sulfate, propylene glycol, stearyl alcohol and white petrolatum, for example, or an ointment containing cetyl esters wax, white wax, almond oil, sodium borate, stronger rose water, and rose oil, for example. Water soluble ointments and creams for use in the present invention may include glycol ethers and derivatives thereof, polyethylene glycols, polyoxyl 40 stearate, and/or polysorbates.

The preparations as described herein for topical applications may also include protectives and absorbents, demulcents such as benzoin, hydroxypropyl cellulose, hydroxypropyl methylcellulose, polyvinyl alcohol, propylene glycols, sodium alginates, and tragacanth. Emollients, astringents, or antiperspirants may also be included in the keratin containing formulations as described herein.

An aspect of the present disclosure is a method for augmenting soft tissue in a subject comprising injecting a keratin composition as described herein subdermally in an area in need of augmentation. A variety of such applications are available in light of the present disclosure and would include augmentation of soft tissue including, but not limited to bulking of a urinary sphincter in order to alleviate urinary incontinence, augmentation of vocal chords to restore elasticity, as well as improvement of the appearance of a subject by augmentation of breasts, lips, chin, gluteal area, or even to improve wrinkled or acne scarred skin, or skin scarred by other conditions, and including soft tissue voids or indentations. A keratin composition may be provided as a dry solid and hydrated after subdermal implantation, or a hydrogel or viscoelastic hydrogel may be prepared and implanted. In certain embodiments, a dry or hydrated keratin material may be contained in a biocompatible envelope, bag, or container for subdermal implantation, and hydrated after implantation by addition of water or absorption of body fluids, or a keratin material may be suspended in an injectable carrier and injected in the desired area of augmentation.

It is an aspect of the present invention that a keratin composition as described herein, and in particular keratin obtained from human hair is also useful as an excipient for the delivery of a pharmaceutical agent, and in particular in the sustained or delayed release of a pharmaceutical agent. An embodiment of the invention may be described, therefore, as a composition comprising a keratin having oxidized cysteic groups and a pharmaceutically active agent. Such a formulation may include a hydratable keratin solid excipient, or a keratin hydrogel depending on the particular application.

In the practice of the invention, a dry hydratable keratin as described herein may be mixed with a powdered pharmaceutical agent and water added to hydrate the mixture, or alternatively such a solid mixture may be formulated as a compressed tablet to be orally administered or for extemporaneous preparations for injection, or as a molded tablet, or it may be enclosed in a capsule for oral administration or subdermal implantation, for example. In certain embodiments a solution containing a water soluble drug or pharmaceutical agent may be added to a hydratable keratin so that the agent is carried into a hydrogel along with the water. A prepared hydrogel, or dry formulation may also be enclosed in a digestible or biodegradable capsule, such as a hard gelatin capsule for oral administration. In certain embodiments, the described pharmaceutical preparations may be formulated for injection, either intravenous, subcutaneous, or intramuscular, for example, or for inhalant, for eye, ear, or nose drops, or for administration as a suppository.

In certain embodiments an active pharmaceutical agent may be associated with a keratin excipient by non-covalent attraction or association, through electrostatic, hydrophobic or ionic interaction, for example, or it may be covalently attached to a keratin excipient by covalent bonding to an oxidized keratin as described herein. In certain embodiments an active agent such as a drug is physically or sterically entrapped within a keratin hydrogel and released over time by diffusion, or as a keratin excipient is degraded.

It is understood that the pills formulated for oral administration, including a hydratable keratin solid, or even pills, capsules or tablets containing a keratin hydrogel may contain ingredients to serve as coatings, additional fillers, binders and for color coding purposes. These ingredients are in common use in present pharmaceutical formulations and may include, but are not limited to, gelatin, lactose, corn starch, calcium phosphate, povidone, magnesium stearate, stearic acid, colloidal silicon dioxide, hydroxypropyl methylcellulose, polyethylene glycol and one or more of the following dyes: FD&C Blue No. I Lake, FD&C Blue No.2 Aluminum Lake, D&C Green No. 5, D&C Yellow No. 10, FD&C Yellow No. 6 or FD&C Red No. 3. Of course these are only exemplary fillers and dyes, those of skill in the art will recognize that other inactive ingredients may be used in the preparation of the formulations of the present invention.

Keratin excipient preparations as described herein may be prepared for oral administration, and would also include injectable solutions or suspensions for intramuscular or subcutaneous implantation including long acting injections, suppositories, topical ointments and transdermal applications such as skin patches. Other ingredients may include a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. The carrier can be a solvent or dispersion medium containing, for example, water, ethanol, polyol (for example, glycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Suitable pharmaceutical agents for use with the excipients described herein would include any pharmaceutical agent that can form an association with the keratin formulations through non-covalent, covalent, or steric; interaction. These agents would include protein therapeutic agents, such as growth factors. In regard to oral administration, such agents may include compounds such as such as acetaminophen, tetracyclines, penicillins, vitamins, antacids, non-steroidal antiinflammatory agents, anesthetics, breath fresheners, and minerals, for example.

In those embodiments in which transdermal administration is desired, the disclosed compositions may be formulated to be administered by use of a skin patch, or transdermal delivery system. Transdermal administration may be accomplished by any of a number of systems known in the art. Examples of systems that may be adapted for use with the compositions described herein include those systems of transdermal administration described in U.S. Pat. Nos. 4,816,252; U.S. Pat. No. 5,122,382; U.S. Pat. No. 5,198,223; U.S. Pat. No. 5,023,084; U.S. Pat. No. 4,906,169; U.S. Pat. No. 5,145,682; U.S. Pat. No. 4,624,665; U.S. Pat. No. 4,687,481; U.S. Pat. No. 4,834,978; and U.S. Pat. No. 4,810,499 (all incorporated herein by reference.)

These methods typically include an adhesive matrix or drug reservoir system and may include a skin permeation enhancement agent such as ethanol, polyethylene clycol 200 dilaurate, isopropyl myristate, glycerol trioleate, linolenic acid saturated ethanol, glycerol monooleate, glycerol monolaurate, n-decyl alcohol, capric acid, and certain saturated and unsaturated fatty acids, and their esters, alcohols, monoglyceride, acetate, diethanolamides and N,N-dimethylamides (See for examples, U.S. Pat. No. 4,906,169).

The release rate of a keratin excipient preparation is determined by the rate at which water is absorbed and the keratin solid disintegrates. The water absorption rate of the solid keratin can be controlled by the number of sulfonic acid residues generated in the oxidation procedure. By exposing the keratin source material to extremes of oxidant concentration, temperature, and time, extremes of absorption rate can be obtained. For example, at low oxidant concentration, colder temperatures and short time periods, relatively few disulfide residues will be converted to sulfonic acid residues. Such a keratin solid, further processed as described herein will absorb relatively little water and disintegrate relatively slowly. Conversely, a keratin solid prepared at high oxidant concentration, at boiling temperature for a long time period, further processed as described herein, will absorb relatively large amounts of water and disintegrate relatively quickly. Disintegration rates between these extremes can be obtained by processing the keratin source material using intermediate conditions.

In some embodiments of the invention, a composition for the delivery of pharmaceutical agents is in the form of a nonwoven film comprising a synthetic polymer and a keratin material. The synthetic polymer may be, but is not limited to, (α-olefins, acrylates, urethanes, acetates, nylons, esters, and copolymers thereof. In some embodiments the nonwoven composition is a laminate, which may be a tri-laminate comprising two outer layers of synthetic polymer and a middle layer of keratin material. The keratin material in the middle layer may be partially exposed by openings in the two outer nonwoven synthetic polymer layers. In some embodiments of the invention the synthetic polymer layers are nonwoven synthetic polymer webs. The nonwoven film pharmaceutical delivery composition may be used externally or internally.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments herein.

DETAILED DESCRIPTION OF THE INVENTION

Figure 1:
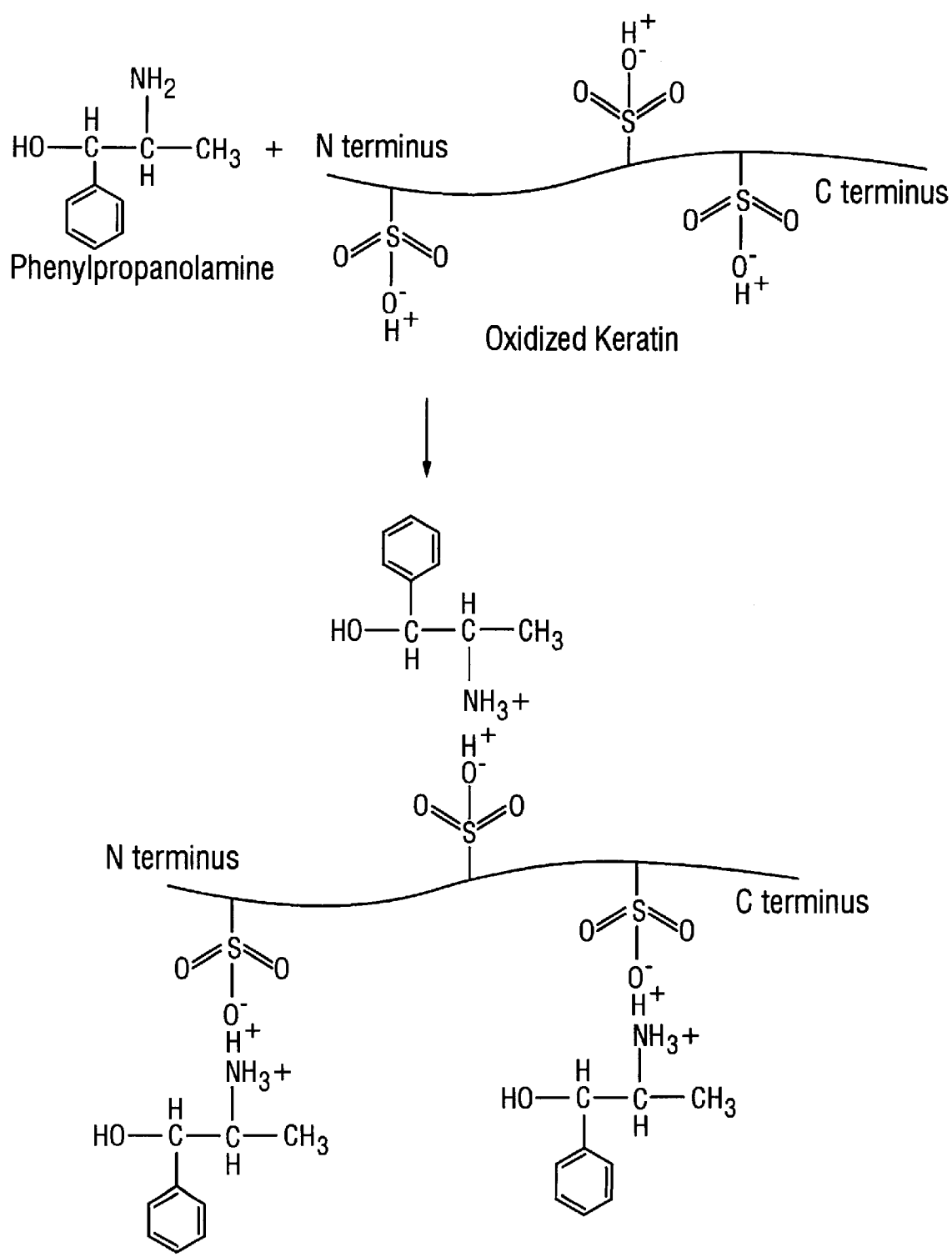
FIG. 1. Schematic of the binding of phenylpropanolamine to oxidized keratin by ion exchange.

The present invention includes a hydratable solid derived from keratin which is highly absorbent and can form a hydrogel or viscoelastic hydrogel upon the application of water. The keratin solid can include protein having an ionizable pendant group such as sulfonic acid which can be derived from an oxidized protein disulfide linkage. A preferred source of protein is keratin, and particularly preferred is keratin obtained from hair, including human hair. While hair is a preferred source of keratinous material, other keratinous materials are also believed suitable for use in the present invention. Examples of other sources include animal hair, skin, hooves, feathers, beaks, feet and horns. The patient or a human donor are some preferred sources of hair, as hair from these sources is most likely to result in a non-immunogenic product, although animal hair may be acceptable for many individuals for many applications. In one method according to the present invention, hair is provided, preferably clean and unbleached. In another method, the hair is washed with Versa-Clean™ (Fisher Scientific, Pittsburgh, Pa.), rinsed with deionized water, and allowed to dry.

A. Preparation of Oxidized Keratin

The hair can be oxidized in peracetic acid or another suitable reagent such as $H_2O_2$. One method utilizes between about 1% to 32% peracetic acid, at a temperature between about 0 degrees C. and 100 degrees C. for between 0.5 and 24 hours. In one method, about 1 weight/volume percent peracetic acid is used. One method treats 30 grams of hair with 500 mL of 4% peracetic acid at 4 degrees C. for 24 hours. Another method treats the hair at room temperature for 24 hours. Yet another method treats the hair at about 90 degrees C. for about 10 hours. In a preferred method, the hair is treated by heating the hair in the oxidizing agent for between about 1 and 4 hours at a temperature between about 20 and 100 degrees C. In a more preferred method, the hair is treated by heating the hair in the oxidizing agent for between about 1 and 2 hours at a temperature between about 80 and 100 degrees C. In a most preferred method, the hair is treated by heating the hair in about 2 weight/volume percent oxidizing agent for about 2 hours at a temperature of about 100 degrees C. The oxidation is believed to cleave a significant portion of keratin disulfide bonds forming cysteic acid residues having sulfonic acid groups. The sulfonic acid groups are believed to be hydrophilic in nature and will ionically bond to cations later in the process, forming a salt of the keratin and cation. The partial oxidation is also believed by Applicants to form short chain peptides, which can remain associated with, or entrained in the keratin structure.

After oxidation, the keratin solid can be recovered from the oxidizing liquid using filtration or other suitable methods such as centrifugation or decantation. The recovered, oxidized solid can be washed with water or alcohol such as methanol or ethanol to remove the excess oxidizing agent. In a preferred embodiment, washing is limited to avoid removing too much of any soluble peptide chains entrained in the keratin.

B. Preparation of Hydratable Keratin

The solid fraction can be suspended in a suitable solvent or solvent mixture. The solvent should be capable of at least suspending the hair or keratin solid and keeping the solid sufficiently swelled for subsequent reaction. The solvent is preferably a non-aqueous solvent, as the presence of water can act to hydrolyze peptide backbone bonds, which can result in an inferior product. The solvent should be able to solubilize the later added base. One group of suitable solvents includes alcohols such as methanol and ethanol. Other solvents such as ether, tetrahydrofuran (THF), acetone, propylene glycol, 1,4-dioxane and glycol ethers may also be suitable as solvents. Small amounts of water will assist in swelling the keratin and may therefore be added to the aforementioned solvents in an amount up to 20 volume percent. The solvent used is preferably volatile to promote evaporation from the final solid product.

The hair or keratin solvent suspension can then have the pH titrated upward to at least about pH 7. Increasing the pH deprotonates the sulfonic acid groups, leaving the sulfonic acids free to exchange with another cation. The pH can be adjusted with a base, preferably having a monovalent cation. Preferred bases include sodium hydroxide and potassium hydroxide.

The pH-adjusted keratin suspension can be heated for a time and temperature sufficient to swell the keratin structure and promote neutralizing of the sulfonic acid sites with the provided cation. In a preferred method, the keratin suspension is boiled between about 0.5 hours and 12 hours. More preferably, the keratin suspension is boiled between about 0.5 hours and 3 hours. In one method, the keratin suspension is boiled for about 1 hour. Boiling for too long a time period leads to a mushy keratin which results from degradation of the peptide backbone. A hydrated keratin product is less preferred due to the greater difficulty of grinding the keratin.

After boiling, the keratin is preferably allowed to continue to react with the provided base cation at lower temperature and with stirring. The lower temperature reaction preferably takes place at a temperature of between about 15 and 30 degrees C. for between about 1 and 24 hours. More preferably, the lower temperature reaction takes place at a temperature of between about 20 and 25 degrees C. for between about 1 and 5 hours. In one method, the keratin suspension is allowed to react with stirring at room temperature for about 5 hours. In certain embodiments the reaction is held at the boiling point of the solvent for about 2 hours.

After reacting at lower temperature, the reacted solid can be separated from the solvent using any suitable method such as filtration. The solid is preferably washed with a solvent such as the same solvent used in the reaction. Washing the keratin removes some of the base, which is preferably removed. The base is preferably removed to make the keratin solid less caustic.

After filtration and washing, the keratin can be dried by a method such as evaporation under vacuum. In one method, the keratin is dried at room temperature under about 5 mm Hg vacuum for about 2 hours. The dried keratin is preferably somewhat brittle, which can result in a better product after grinding. The dried keratin can be shredded into fibers and can further be ground into a powder. The dried keratin can be directly ground into a powder using a mortar and pestle, a ball mill, or other means of breaking down or comminuting the dried keratin into particles. Alternatively, the keratin can be ground or milled in the solvent used for said neutralization step.

One resulting hydratable fiber or powder has been observed to absorb about 10 to 13 times its own weight in water. In one test, fibers having a length of between one quarter and one-half inch were observed to absorb an average of 1300%+/−33% of their weight in water at a temperature of 21.5 degrees C. The fiber has been observed to absorb at least 10 times its own weight in water within about 10 seconds. The powder has been observed to rapidly absorb water as well.

The fibers were also tested for various toxicity parameters and were found to be non-toxic, non-irritating, non-sensitizing as indicated in Table 1.

TABLE 1

Hydratable Keratin Toxicity Testing Data

| Test | Standard Protocol | Result |
| --- | --- | --- |
| Acute Oral Toxicity | Biological Evaluation of Medical Devices - Part 11: Tests for Systemic Toxicity; ISO 10993–11, 1993. | Non-toxic at 2 g/kg |
| Acute Dermal Toxicity | Biological Testing of Medical and Dental Materials and Devices - Part 10: Irritation and Sensitization Tests; ISO 10993–10, 1995. | Non-toxic at 2 g/kg |
| Acute Irritation | Biological Testing of Medical and Dental Materials and Devices - Part 10: Irritation and Sensitization Tests; ISO 10993–10, 1995. | Non-irritating at 33.3 wt. % |
| Kligman Sensitization | Biological Testing of Medical and Dental Materials and Devices - Part 10: Irritation and Sensitization Tests; ISO 10993–10, 1995. | Non-sensitizing at 33.3 wt. % |
| Material Mediated Pyrogen Assay | Biological Evaluation of Medical Devices - Part 11: Tests for Systemic Toxicity; ISO 10993–11, 1993. | Passed |
| Systemic Injection | Biological Evaluation of Medical Devices - Part 11: Tests for Systemic Toxicity; ISO 10993–11, 1993. | Passed |

C. Preparation of Nonwoven Films

1. Nonwoven Film Comprising Film Hydratable Keratin

Hydratable keratin fibers may be incorporated into a nonwoven film by admixing with synthetic fibers which serve as a binder. Such a nonwoven film can be formed by mixing synthetic fibers made from, but not limited to, (α-olefins, acrylates, urethanes, acetates, nylons esters, or copolymers thereof with water-absorbent keratin fibers and heat pressing the mixture into a film of desired thickness. The synthetic fibers will serve as a binder for the keratin fibers, while not completely encapsulating them. This morphology provides mechanical integrity to the film, while allowing the keratin fibers to absorb water. The hydrated fibers can also release material which has been shown to be beneficial for repairing damaged epithelial tissue.

Nonwoven films can be prepared by preparing nonwoven webs of a synthetic polymer and then placing a layer of hydratable keratin fibers between two layers of the nonwoven polymer-web. For example, a nonwoven film was produced by first preparing a nonwoven web measuring approximately one half inch thick by 24 inches wide using 9 denier, 38 mm length polypropylene fibers. The web was made using a Rando-Webber, (Fiber Controls, Inc. Gastonia, N.C.) air laying machine operating at 2000 rpm, 12 ft./minute let off speed with a feed rate of 4 ft./minute. A web of approximately 20 feet in length was coated over half of its length on one side with keratin fibers of approximately 2–5 mm in length. The keratin was spread on the web using a hand sifter. The uncoated section of the web was folded back over the coated section to form a laminate of keratin between two layers of polypropylene. The laminate was passed through a Sigma heated roller press (BF Perkins, Rochester N.Y.). The rolls were oil heated to 160° C. and a pressure of 350 pounds per linear inch was applied. The surface of the top roller was textured so as to impress a texture in the finished nonwoven film. The laminate was fed through the rollers at approximately 4 ft./minute and the polypropylene softened and pressed such that a film of approximately 3 mm in thickness resulted. This nonwoven film was bound together by the polypropylene, but retained some flexibility. The keratin fibers were at least partially exposed such that the film wetted easily and the keratin became gelatinous upon addition of water.

Nonwoven films can be made by other procedures. For example, if a more open nonwoven is desired, a laminate of keratin and synthetic fibers can be prepared as described above, and this laminate processed by a through air dryer. The through air dryer is capable of heating the laminate but does not apply pressure to the film. In this process, the synthetic fibers can be softened and bound together, thus providing a structural matrix for the keratin fibers. The result is a nonwoven web which retains more of its original, open morphology. Also, films made with synthetic fibers can sometimes be stiff. The example given above resulted in a film resembling burlap. If a softer film is desired, alternative fibers or blends of fibers may be used to produce the nonwoven web. A blend of cotton and polypropylene, for example, would provide a softer, more pliable nonwoven film. Cotton fibers can conveniently be blended into the nonwoven web during the air laying or carding process, prior to coating with keratin fibers. Other natural fibers such as hemp may also be used.

These nonwoven films are produced from a loose, laminated precursor. However, the keratin fibers are exposed to the surface in the final product. Although the exemplified polymeric binder is hydrophobic, the nonwoven film wets easily and readily absorbs water. Once water is applied to the film, the keratin fibers absorb it and swell, thus forming a hydrogel which is entrained in the unswollen binder. This type of film is of utility as a wound dressing because of the capability of absorbing wound exudate and forming a hydrated, gelatinous cover over the wound site. Such a dressing provides a closed, moist environment, conducive to wound healing. Due to the water absorbency, these nonwoven films also have utility as components of disposable diapers, feminine hygiene products as well as any other application where a nontoxic film with biocompatibility and absorbency is desired and the healing of damaged skin or other epithelial tissue is deemed beneficial or necessary.

2. Nonwoven Film Comprising Oxidized Keratin Powder

Nonwoven films can also be prepared with oxidized keratin powder. For example, a nonwoven web measuring approximately one half inch thick by 24 inches wide was prepared using 1.7 denier, 38 mm length Fortrel® polyester fibers supplied from Wellman, Inc. (Johnsonville, S.C.). A blend of 20 wt. % low melt and 80 wt. % high melt fibers was first mixed by hand, then run through a Garnett fine opener, and finally carded. This was done prior to laying the web to provide a homogeneous sample. The web was made using a Rando-Webber (Fiber Controls, Inc, Gastonia, N.C.) air laying machine operating at 2000 rpm, 12 ft./minute let off speed with a feed rate of 4 ft./minute.

The web was mechanically entangled using a hydrobonder from Honeycomb Systems, Div. (Division of Valmet, Inc., Biddeford, Me). This equipment consists of a screen conveyor and a manifold of high pressure waterjets. The web passes under the water jet manifold and the force of the water forces the fibers through the screen, thereby entangling them. The degree of entanglement can be controlled by the mesh size of the screen conveyor. The excess water was removed using a vacuum stripper manufactured by Evac Corporation, (Spartanburg, S.C.). This process reduced the web's thickness to approximately one eighth inch and resulted in a more tightly entangled web with more structural integrity than one produced using only the air laying technique.

Two rolls of web, 20 feet in length, were prepared using this process and used to make a laminate with hydratable keratin powder. The keratin powder was less than 300 μm in size and was prepared as described for keratin fibers. The laminate was prepared by conveying the two webs from separate spools and spraying the powder onto the bottom web. Powder was sprayed using a GEMA™ powder sprayer with an electrostatic spray gun (the electrostatic feature was not used). The gun was operated at 2 psi with a flow of 4.5 m³/hour through the reservoir and a make-up flow of 1.5 m³/hour through the gun. The nonwoven laminate was conveyed with a take-up winder operating at 32 ft./minute. The use of a tighter web allowed small keratin particles (length of less than 1 mm) to be used without significant loss. This was especially important during the winding and unwinding operations prior to thermal bonding. The web could also be moistened slightly prior to spraying the keratin in order to promote adhesion.

The nonwoven laminate was passed through a Sigma heated roller press. The rolls were oil heated to 160° C. and a pressure of 200 to 215 pounds per linear inch was applied. The surface of the top roller was textured so as to impress a texture in the finished nonwoven film. The laminate was fed through the rollers at approximately 15 to 17 ft./minute. This procedure resulted in a nonwoven film of approximately 3 mm in thickness. The surface of the film was smoother than the film described previously and the use of polyester, rather than polypropylene, produced a softer, more pliable film. The keratin powder was at least partially exposed such that the film wetted easily and the keratin became gelatinous upon addition of water.

D. Nonwoven Film Drug Delivery Systems

Pharmaceutical agents can be incorporated into solid keratin to form a drug delivery system. Pharmaceutical agents that can be incorporated into solid keratin include, but are not limited to, compounds that may ion exchange with sulfonic acid groups identified as those compounds that may otherwise be formulated as hydrochlorides, polar agents, protein agents, polypeptide agents and peptide agents. Protein agents include both recombinant and native proteins. Polar compounds include, but are not limited to 4-acetaminophenol, aspirin and beta-lactams. Compounds that may otherwise be formulated as hydrochlorides include, but are not limited to phenylpropanolamine and pseudoephedrine. Other examples of pharmaceutical agents that may be formulated as hydrochlorides are found in Remington: The Science and Practice of Pharmacy, (19th ed., ed. A. Gennaro) 1995, herein incorporated by reference in its entirety. A non-exhaustive list that exemplifies some of the classes and types of pharmaceutical agents that may be used in the present invention is provided in Table 2.

TABLE 2

| | |
|---|---|
| Analgesics | aspirin, acetaminophen, morphine, oxymorphone, codeine, oxycodone |
| Antianxiety Drugs | buspirone, benzodiazepine, venlafaxine |
| Antiarrhythmics | flecainide, encainide, lidocaine, digoxin, beta-blockers, procainamide |
| Antibacterials | beta-lactams, aminoglyopsides, macrolides, clindamycin, tetracylin, quinolones, sulfonamides, trimethoprimsulfamethoxazole, sulfisoxaole, sulfasalazine, |
| Antibiotics | penicillins cephalosporins, amnioglycosidases, macrolides, fluroquniolones, chloamphenicol, rifampin, vancomycin |
| Anticonvulsants | phenytoin, ethosuximide, valproate, diazepam |
| Antifungals | amphotericin B, clotrimaozole, econazole, fluconazole, flucytosine, griseofulvin, haloprogrin, ketoconazole, itraconazole, miconazole, nystatin, tolfanate, undecylenic acid, terconazole, triacetin |
| Antihistamines | alkylamines, ethanolamines, ethylenediamines, piperazines, phenothiazines, piperidines |
| Anti-Inflammatories | betamethasone dipropionate, clobetasol propianate, amcinonide, halcinonide, fluocinolone acetonide, betamethasone alerte, flubiprofen, ibuprofen, indomethacin, ketoprofen, mefenamic, naproxen, phenylbutazone, suldinac |
| Antivirals | acyclovir, amantidine, didanosine, inosiplex, intrathecal, ribavirin, ganciclovir, triflurdine |
| Cytotoxics | prednisolone, azathioprine, cyclophosphamide, cyclosporine, tacrolimus |
| Cytokines | inteferon alpha, interferon beta, colony stimulating factors (GM-CSF, M-CSF, G-CSF), interleukins 1 through 11, tumor necrosis factor beta |
| Growth Factors | platelet-derived growth factor, epidermal growth factor, fibroblast growth factor, insulin-like growth factors, transformin growth factor beta |
| Muscle Relaxants | benzodiazepines, imidazopyridine, diphenhydramine, pyrilamine |
| Sympathomimetics | phenylpropanolomine, phenylephrine, psudoephedrine |
| Vitamins | A, $B_6$, $B_{12}$, C, D, E, folacin, thaimin, riboflavin, niacin, pantothenic acid, biotin |

The drug delivery system of the present invention offers distinct advantages over conventional drug dosage forms. As with most delivery systems, sustained or controlled release allows the level of a drug to be maintained at a more consistent concentration, thereby allowing larger doses to be administered on a less frequent basis. In the system described here, the chemical and material properties of the keratin determine the properties of the dosage form. For example, loading can be varied by the availability of sulfonic acid binding sites, which can in turn be controlled by the keratin oxidation process. Further, the disintegration and breakdown of the keratin can also be controlled by the relative amount of disulflide crosslinks remaining after the oxidation process. Disintegration and dissolution will effect the release kinetics of the dosage form. When incorporated into a nonwoven wound dressing, the bound drugs can be tailored to those most beneficial to wound healing such as, for example, antibiotics, biocides, pain medications and growth factors.

Another advantage of this system is in its application to different drug compounds. Non-water soluble drugs, for example, are typically troublesome to formulate into convenient dosage forms. Non-water soluble drugs are particularly suited to the ion exchange process with keratin, however, because this process is preferably performed in non-aqueous media. Keratin also offers the advantage of biocompatibility and lack of toxicity. Keratin can also perform the dual role of wound dressing and delivery system, thereby providing a less invasive therapy than separate treatments.

The loading of keratin with a drug molecule is not limited to specific binding with sulfonic acid residues. Many potential sites exist on keratin polypeptides which can provide acid-base interactions useful for additional loading of molecules with complementary structures. The binding energies of these groups would be lower and therefore, these molecules would be more readily available for bioabsorption. By saturating the sulfonic acid sites, an excess of drug molecules could be bound through non-specific interactions so as to provide an initial release of the drug. Sustained release would be provided by binding groups requiring more energy for disassociation. These types of release kinetics would be useful for conditions requiring pain relief, for example.

Following are examples of preparation and dissolution testing of nonwoven hydratable keratin drug delivery systems:

1. Albumin

Albumin may be used as a prototypical protein pharmaceutical agent. A mixture of albumin and hydratable keratin is prepared by co-grinding a mixture, for example 80/20, of powdered hydratable keratin and bovine albumin. Albumin may be purchased from Sigma Chemical Co., St. Louis, Mo. (Fraction V, 96% purity). The solid mixture is further homogenized by shaking in a closed container. The mixture is applied to a nonwoven polymer web as described in Section C. 1 supra.

2. Phenylpropanolamine (Norephedrine)

Figure 2:
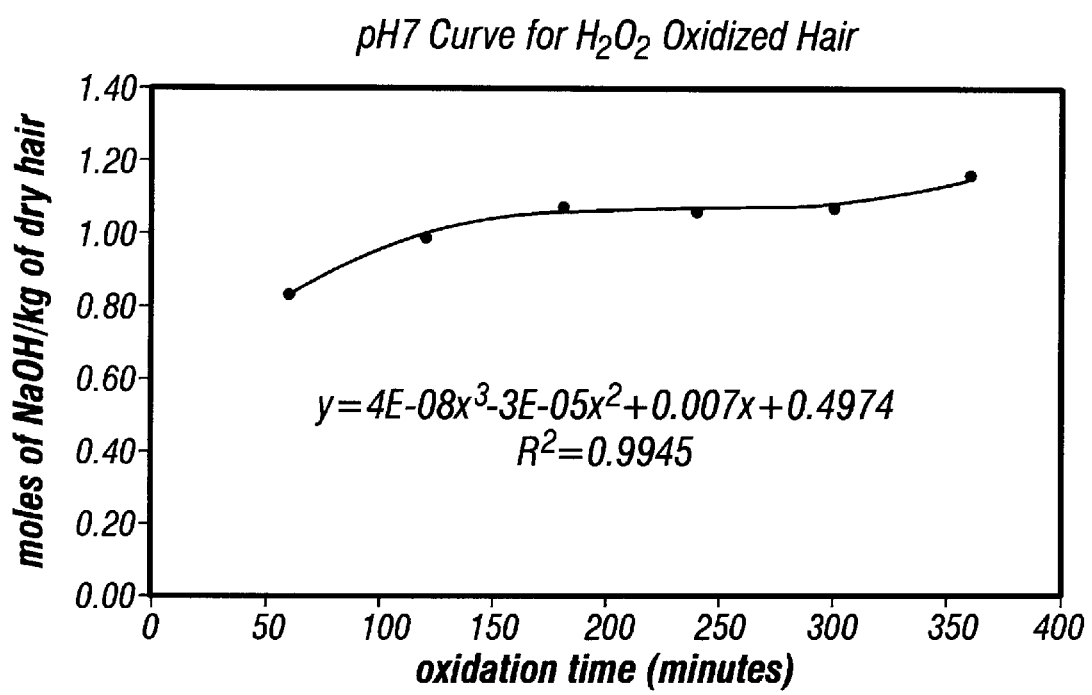
FIG. 2. Titration curve for hair oxidized by hydrogen peroxide.

Samples are prepared by binding the norephedrine to oxidized keratin in an ion exchange step. For example, six different oxidized keratin samples are prepared by boiling 30 g each of human hair in 500 mL of 2 w/v % $H_2O_2$ for 1, 2, 3, 4, 5 and 6 hours. This will generate samples with different amounts of sulfonic acid residue, hence, different binding affinities and consequently, different release characteristics. Each of the oxidized keratin samples is ion exchanged with oxidized keratin by the mechanism shown in FIG. 1. This is accomplished by dissolving a measured amount of norephedrine into ethanol, adding 5 g of oxidized keratin and heating to reflux for 2 hours, followed by stirring at room temperature for 24 hours. Measured amounts of norephedrine are determined based on the amount of time the hair had been oxidized. For example, 5 g of hair oxidized for 4 hours will be exchanged with approximately $5 \times 10^{-3}$ moles of norephedrine. This calculation is based on data generated for a pH 7 titration curve for $H_2O_2$ oxidized hair which is shown in FIG. 2.

After binding the norephedrine in the ion exchange step, the solid keratin is separated by filtration, dried, ground and applied to a nonwoven polymer web as described in Section C.1 supra.

3. 4-Acetaminophenol (Acetaminophen)

Samples incorporating the antipyretic acetaminophen arc prepared by binding the drug to oxidized keratin in an ion exchange step. For example, six different oxidized keratin samples are prepared by boiling 30 g each of human hair in 500 mL of 2 w/v % $H_2O_2$ for 1, 2, 3, 4, 5 and 6 hours. This will generate samples with different amounts of sulfonic acid residue, hence, different binding affinities and consequently, different release characteristics. Compounds with weak ability to form amine salts, such as acetaminophen are expected to form acid-base interactions with keratin molecules. This binding is similar to the ion exchange process described for norephedrine, but results in a less tightly bound drug. Acid-base binding is accomplished by dissolving a measured amount of acetaminophen into ethanol, adding 5 g of oxidized keratin and heating to reflux for 2 hours, followed by stirring at room temperature for 24 hours. Measured amounts of acetaminophen are estimated based on the amount of time the hair had been oxidized. The pH 7 titration curve for $H_2O_2$ oxidized hair, shown in FIG. 2, is used to calculate minimum number of binding sites, assuming that there were sites other than sulfonic acid residues which were capable of acid-base interactions.

After binding the acetaminophen in the ion exchange step, the solid keratin is separated by filtration, dried, ground and applied to a nonwoven polymer web as described in Section C.1 supra.

4. Dissolution Testing

(a) Franz Diffusion Cell

Dissolution tests of the preceding formulations for topical application may be performed using one-chambered Franz type diffusion cells (Franz, 1978). Franz cells may be obtained from Crown Glass (Somerville N.J.). In these cells, one side of a membrane is in contact with an aqueous solution and the other side is open to the ambient atmosphere, unless placed within a controlled atmosphere. The nonwoven keratin film is mounted in the diffusion cell such that one side is in direct contact with the aqueous receptor solution (Lee et al., 1986). The aqueous solution is continuously stirred and kept at 32° C. by means of a water jacket.

Samples are removed from the aqueous medium by means of the sampling port at appropriate times. For example, samples may be taken every 20 minutes within the first hour (including a zero time point) and every hour after that for 8 hours. An additional sample may be taken at 24 hours. High-performance liquid chromatography (HPLC) or other suitable analytical quantification is performed on the samples and the amount released from the dosage form is calculated based on a calibration curve generated from solutions of known concentrations.

(b) Rotating Paddle Method

Dissolution tests may be performed according to the standard United States Pharmacopoeia (USP) rotating paddle method (United States Pharmacopeia: United States Pharmacopeia Convention Inc., 1995). In this method, the volume of the dissolution medium is fixed and agitation is provided under defined conditions by the stainless steel paddle. A 1L volume of deionized water is used and the test is conducted at 37° C.±0.5° C. for evaluating the nonwoven delivery system for internal applications and 32° C.±0.5° C. for examining the evaluating topical applications. The temperature of the dissolution medium is maintained at constant temperature by immersing the dissolution flask in a water bath. A cover is used on the system to avoid water loss through evaporation. After the temperature has equilibrated, the nonwoven samples are introduced and the paddle is turned on. The nonwoven film sample may be placed in a stainless-steel disc assembly to hold the sample at the bottom of the vessel. Rotation is smooth and the speed was kept constant at 50rpm.

During the test, small volumes of sample are withdrawn at appropriate time points, for example, every 20 minutes within the first hour (including a zero time point) and every hour after that for 8 hours. An additional sample may be taken at 24 hours. Samples are taken from a precise point in the dissolution flask, halfway between the surface of the dissolution medium and the top of the rotating paddle, and not less than 10 mm from the wall of the vessel. The volume withdrawn during sampling is replaced with an equal volume of deionized water, pre-warmed to 37° C. High-performance liquid chromatography (HPLC) or other suitable analytical quantification is performed on the samples and the amount released from the dosage form is calculated based on a calibration curve generated from solutions of known concentrations.

E. Applications of Hydratable Keratin

One use for the keratin powder and fiber is as a disposable diaper filler material. Disposable diapers typically have an absorbent inner layer which is often filled with a superabsorbent polymer and cellulosic material, often chemically derived from wood pulp. In one application of the keratin material, a layer of the hydratable keratin is positioned in a disposable diaper near the skin but separated from the skin by a permeable layer. The hydratable keratin layer can serve to absorb urine and water from the wearer. In some embodiments, the hydratable keratin includes a substantial fraction of soluble peptides having wound healing properties, as discussed in co-pending U.S. pat. application Ser. No. 09/330,550, filed Jun. 11, 1999, entitled SOLUBLE KERATIN PEPTIDE, herein incorporated by reference. The water-soluble peptides are believed to be entrained in the keratin structure and able to leach out when water is applied. In use, the keratin layer remains dry until soaked with urine, at which point the soluble peptides can diffuse out of the keratin. The soluble peptides dissolved in the liquid present can thus come in contact with the skin. The wound healing properties of the peptides are believed to be beneficial in treating diaper rash.

In another use, the hydratable keratin powder or fiber can be used as an ingredient in cosmetics. In one application, the keratin powder is admixed with other cosmetic ingredients. The keratin power, when brought into contact with water from the other cosmetic ingredients or from the skin of the wearer, forms a hydrogel which forms a protective layer over the skin and also retains moisture against the skin. The keratin powder, which has beneficial properties for skin, is thus held against the skin, moisturizing the skin. In some embodiments, the keratin powder includes soluble peptides which can diffuse out of the powder with application of water. The soluble peptides are believed to be non-immunogenic, mitogenic, and have beneficial skin healing properties. Cosmetics including the hydratable keratin powder can aid in both moisturizing and healing skin. Keratin powder can also be used as an absorbent replacement to talc, the most popular cosmetic base, to which many are allergic. The keratin powder or fibrous material can be used to promote healing of damaged skin. The keratin material can be applied to skin afflictions such as diaper rash, burns, sunburns, cuts, abrasions, punctures, sores, bed sores, ulcers, diabetic ulcers, irritated skin, surgical incisions, skin graft donor sites, and wrinkled skin. In one method, the keratin material is admixed with a carrier such as a cream, lotion, or gel.

Other applications of the keratin solid include using the keratin powder or fibers in feminine hygiene products, where the keratin can serve a moisture absorbing function. Yet another application is in antiperspirants, where the keratin solid can absorb moisture. Still another application is in drug release applications, where the keratin can be used in powder, fiber, or film form to provide a moist, benign environment against the skin for drug release. The present invention, in powder, fiber, and nonwoven sheet forms, is also believed suitable for use in forming tissue-engineering scaffolds. An additional use as a food additive is contemplated, as some naturally-derived products, such as gelatin, are already used in food products.

The keratin can also be used as the precursor to the formation of a gel, which can form a keratin hydrogel upon the addition of water to the absorbent keratin solid. The keratin can be used to form an in situ gel. In the in situ application, the keratin powder can reside within an envelope predisposed at a site and the water added into the envelop already in position. The keratin can be stored in solid form, for example as a fiber, powder, or some combination thereof, and water added later. Keeping the keratin in solid form allows for storage and later gel formation only when desired, as in an emergency medical field dressing application. Requiring the keratin to pass through a solid step also serves to purify the resulting gel, as many impurities are removed in the intermediate processing steps.

The present invention can also be used to augment soft tissue. Keratin hydrogel precursor in powder form may be suspended in an injectable carrier and injected subdermally. In one method, the keratin powder is suspended in saline and injected subdermally.

The resulting hydrogel has been observed to have viscoelastic properties, favorable for use as an implant filler such as a breast implant. The hydrogel has been observed to flow more readily when manipulated, which may prove beneficial to implant applications where the consistency of the implant is important.

The present invention can be used in a wound dressing. One use of hydratable keratin in a wound dressing is wound exudate management. Thus hydratable keratin may be used as a component of an absorbent wound dressing. In one embodiment, the hydratable keratin may be used in the form of a nonwoven film. In another embodiment, hydratable keratin may be used as a woven composition. In a woven composition, fibers of hydratable keratin may be woven with natural fibers or synthetic polymer fibers. In another embodiment, hydratable keratin is enclosed by a water-permeable material which, while allowing passage of wound exudate and blood, prevents passage of the hydratable keratin solid of the present invention. Wound dressings include, but are not limited to, adhesive bandages and tapes.

Skin-contact adhesive bandages and medical tapes are well known to those of skill in the art. Adhesive bandages typically comprise an absorbent pad, a backing and a pressure sensitive adhesive to maintain the dressing in place. In one aspect of the present invention, an absorbent wound dressing comprising hydratable keratin is an absorbent pad of an adhesive bandage. Components, configurations and delivery systems for adhesive bandages are disclosed in U.S. Pat. Nos. 6,018,092, 5,947,917, 5,633,070, and 5,503,908, which are herein incorporated by reference. Upon contact with moisture, which may be in the form of wound exudate or blood, the keratin fibers can form a hydrogel and leach water soluble peptides into the wound.

Numerous advantages of the invention covered by this document have been set forth in the foregoing description. It will be understood, however, that this disclosure is, in many respects, only illustrative. Changes may, be made in details, particularly in matters of reagents, concentrations, and step order, without exceeding the scope of the invention. The invention's scope is, of course, defined in the language in which the appended claims are expressed.

REFERENCES

Franz, "The finite dose technique as a valid in vitro model for the study of percuatenous absorption in man", *Curr. Probl. Dermatol.*, 7:309, 1978.

Lee et al., "Kinetics and thermodynamics of drug permeation through silicone elastomer III. Effect of alkyl substituent (R) in (MeRSIO)$_x$ polymer", *Drug Dev. Indust. Pharm.*, 12:349, 1986.

What is claimed is:

1. An absorbent wound dressing comprising a hydratable keratin solid wherein said hydratable keratin comprises keratin having sulfonic acid groups ionically associated with monovalent cations.

2. The absorbent wound dressing of claim 1, wherein said monovalent cations are potassium or sodium cations.

3. The absorbent wound dressing of claim 1, wherein said hydratable keratin is obtained from hair, feathers, fur, skin, nails, beaks, horns or hooves.

4. The absorbent wound dressing of claim 3, wherein said hair is human hair.

5. The absorbent wound dressing of claim 1, wherein said absorbent wound dressing is the absorbent pad of an adhesive bandage.

6. The absorbent wound dressing of claim 1, wherein said hydratable keratin is in a nonwoven film comprising a synthetic polymer and said hydratable keratin.

7. The absorbent wound dressing of claim 6, wherein said nonwoven film composition is a laminate nonwoven film composition.

8. The absorbent wound dressing of claim 7, wherein said laminate is a tri-laminate comprising two outer layers of said synthetic polymer and an middle layer of said hydratable keratin.

9. The absorbent wound dressing of claim 8, wherein said middle layer of hydratable keratin is partially exposed by openings in said two outer synthetic polymer layers.

10. The absorbent wound dressing of claim 6, wherein said synthetic polymer is in the form of a nonwoven-web.

11. The absorbent wound dressing of claim 6, wherein said synthetic polymer is made from a material selected from the group consisting of α-olefins, acrylates, urethanes, acetates, nylons, esters, and copolymers thereof.

12. The absorbent wound dressing of claim 6, wherein said synthetic polymer further comprises a natural material.

13. The absorbent wound dressing claim 1, further comprising a pharmaceutical agent associated with said hydratable keratin.

14. The absorbent wound dressing of claim 7, wherein said laminate nonwoven film composition is made by the process comprising the steps:

a. preparing a first nonwoven web layer comprising said synthetic polymer;

b. applying said hydratable keratin to one surface of said first nonwoven web layer comprising said synthetic polymer;

c. applying a second nonwoven web layer comprising said synthetic polymer to said hydratable keratin applied to said first nonwoven web layer to obtain a tri-laminate composition comprising two outer layers of said first and second nonwoven webs comprising said synthetic polymer and a middle layer of said hydratable keratin.

15. The absorbent wound dressing of claim 1, wherein said hydratable keratin entrains or is associated with water soluble peptides.

16. The absorbent wound dressing of claim 15, wherein at least some of said water soluble peptides leach out from said hydratable keratin upon contacting moisture.

17. The absorbent wound dressing of claim 16, wherein said moisture is provided by wound exudate or blood.

18. The absorbent wound dressing of claim 15, wherein said water soluble peptides promote the healing of damaged skin.

19. The absorbent wound dressing of claim 6, wherein said absorbent wound dressing is the absorbent pad of an adhesive bandage.

20. The absorbent wound dressing of claim 13, wherein said absorbent wound dressing is the absorbent pad of an adhesive bandage.

21. The absorbent wound dressing of claim 15, wherein said absorbent wound dressing is the absorbent pad of an adhesive bandage.

* * * * *